(12) United States Patent
Juo et al.

(10) Patent No.: US 9,315,812 B2
(45) Date of Patent: Apr. 19, 2016

(54) METHODS OF USING MICRORNA 195 IN PROVIDING NEUROPROTECTION

(71) Applicant: KAOHSIUNG MEDICAL UNIVERSITY, Kaohsiung (TW)

(72) Inventors: Suh-Hang H Juo, Kaohsiung (TW); Yung-Song Wang, Kaohsiung (TW); Hsin-Yun Cheng, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 14/354,928

(22) PCT Filed: Nov. 5, 2012

(86) PCT No.: PCT/US2012/063604
§ 371 (c)(1),
(2) Date: Apr. 29, 2014

(87) PCT Pub. No.: WO2013/067531
PCT Pub. Date: May 10, 2013

(65) Prior Publication Data
US 2014/0294943 A1    Oct. 2, 2014

Related U.S. Application Data

(60) Provisional application No. 61/555,152, filed on Nov. 3, 2011.

(51) Int. Cl.
*C12N 15/113* (2010.01)
(52) U.S. Cl.
CPC ........ *C12N 15/113* (2013.01); *C12N 2310/141* (2013.01); *C12N 2310/3231* (2013.01)
(58) Field of Classification Search
CPC .................. C12N 15/113; C12N 2310/141
See application file for complete search history.

(56) References Cited

U.S. PATENT DOCUMENTS

| 2005/0261218 | A1 | 11/2005 | Esau et al. | |
| 2006/0105360 | A1* | 5/2006 | Croce et al. | 435/6 |
| 2010/0298407 | A1* | 11/2010 | Mendell et al. | 514/44 A |
| 2011/0142913 | A1* | 6/2011 | Juo et al. | 424/450 |

FOREIGN PATENT DOCUMENTS

| EP | 2112235 | 10/2009 |
| WO | 2009/120877 | 10/2009 |
| WO | 2010/151640 | 12/2010 |

OTHER PUBLICATIONS

EPO search report for Europen application No. EP12845133.3.
Diana O Perkins et al., microRNA expression in the prefrontal cortex of individuals with schizophrenia and schizoaffective disorder, Genome Biology 2007, 8:R27;1-11.
Nikolaus Mellios et al., A set of differentially expressed miRNAs, including miR-30a-5p, act as post-transcriptional inhibitors of BDNF in prefrontal cortex, Human Molecular Genetics 2008, vol. 17: No. 19 :3030-3042.
Hong-Can Zhu et al., MicroRNA-195 downregulates Alzheimer's disease amyloid-production by targeting BACE1, Brain Research Bulletin 2012, 88: 596-601.
Soon-Tae Lee et al.,MicroRNAs Induced During Ischemic Preconditioning, Stroke. 2010;41:1646-1651.
JPO search report for Japanese application number: 2014-540189 and its English translation.

* cited by examiner

*Primary Examiner* — Jon E Angell
(74) *Attorney, Agent, or Firm* — Hannah M. Tien

(57) ABSTRACT

The invention relates to a method for providing neuroprotection comprising administering to a subject an effective amount of a miRNA or a variant thereof. By providing neuroprotection, stroke or ischemic stroke can be prevented and/or treated.

21 Claims, 11 Drawing Sheets

A

B

C

D

METHODS OF USING MICRORNA 195 IN PROVIDING NEUROPROTECTION

FIELD OF THE INVENTION

The invention relates to a method of providing neuroprotection, comprising administering to a subject an effective amount of a miRNA or a modified microRNA thereof. Particularly, the neuroprotection is directed to treatment and/or prevention of stroke.

BACKGROUND OF THE INVENTION

A key feature of the central nervous system ("CNS") is that differentiated neurons are essentially incapable of regeneration. Permanent loss of function is thus a likely outcome of a sufficiently severe injury or insult to the brain. Accordingly, there is a need for means to protect cells of the central nervous system from death after an injury. Damage to different cell types in the central nervous system, such as, asphyxial, traumatic, toxic, infectious, degenerative, metabolic, ischemic or hypoxic insults, may cause sensory, motor or cognitive deficits.

MicroRNAs (miRNAs) are single-stranded RNA molecules of about 21-23 nucleotides. A miRNA is complementary to the 3' untranslated region (3'-UTR) of one or more messenger RNAs (mRNAs). The annealing of the miRNA to the mRNA causes inhibition of protein translation and/or facilitation of mRNA degradation. Recent studies reveal that miRNAs may play a key role in the process of atherosclerosis by influencing genetic expressions within vascular smooth muscle cells (VSMCs) and endothelial cells (Y. Suarez et al., *Proc. Natl. Acad. Sci. USA* 105, 14082, 2008; L. Poliseno et al., *Blood* 108, 3068, 2006; and X. Liu et al., *Circ. Res.* 104, 476 2009). For example, miR-145 was found to be a VSMC phenotypic marker and regulate vascular neointimal lesion formation (Y Cheng et al., *Circ. Res.* 105, 158, 2009). Elevated plasma levels of several miRNAs were also demonstrated in patients of acute myocardial infarction, suggesting that circulating miRNAs may serve as biomarkers of cardiovascular diseases (Y. D'Alessandra et al., *Eur. Heart J.* 31, 2765, 2010). However, miRNA studies in the context of atherosclerosis are still in the infantile stage.

Xu T et al. indicated that microRNA-195 suppresses tumorigenicity and regulates G1/S transition of human hepatocellular carcinoma cells (Xu T et al., *Hepatology*. 2009 July; 50(1): 113-21). Huaqing Zhu et al. reported that microRNA-195 promotes palmitate-induced apoptosis in cardiomyocytes by down-regulating Sirt1 (Xu T et al., *Cardiovasc Res* (2011) first published online May 27, 2011). Sekiya Y et al. reported down-regulation of cyclin E1 expression by microrna-195 accounts for interferon-β-induced inhibition of hepatic stellate cell proliferation (Sekiya Y et al., *J. Cell. Physiol. Vol.* 226, No. 10, pp. 2535-2542, 2011).

U.S. patent application Ser. No. 12/635,178, filed on 10 Dec. 2009 discloses that microRNA-195 can be used in the treatment of atherosclerosis. Several risk factors can increase a risk for stroke. By reducing these risk factors can prevent stroke. Drug Discovery Today, Volume 17, Numbers 7/8, April 2012, pp. 296-309 states the prevention approaches of stroke. However, the reference also indicates that there are only few effective treatments for acute stroke (see page 299). Those of ordinary skill in the art know the prevention of stroke is not equal to treatment of acute stroke. Additional information for stroke treatment can be found in the website of National Stroke Association (http://www.stroke.org/site/PageServer?pagename=treatment). Therefore, the discovery of miR-195's effect on anti-atherosclerosis can not be extrapolated mir-195's therapeutic effect on acute stroke.

Kandiah Jeyaseelan et al. report that the involvement of miRNA regulation in brain pathogenesis associated with middle cerebral artery occlusion (MCAo) and indicate that comparison with the corresponding DNA microarray data revealed that the target mRNA expression is correlated with the regulation of miRNA (Kandiah Jeyaseelan et al., Stroke, March 2008, pp. 959-966). The reference also reports that some of the miRNAs that are highly expressed in the ischemic brain can be detected in blood samples; for example, microRNA-195 was found at 48-hour reperfusion in both the blood and brain samples. However, microRNA-195 showed an opposite trend in expression. Therefore, even persons skilled in the art would not be able to predict whether microRNA-195 can be neuroprotective or not after ischemic stroke.

Given the above, no prior references teach or suggest the neuroprotection effect caused by increasing an amount of a microRNA-195.

SUMMARY OF THE INVENTION

The invention also provides a method for providing neuroprotection comprising administering to a subject an effective amount of a microRNA selected from a miRNA-195, a modified miRNA-195 and a combination thereof.

In one embodiment, the neuroprotection is through inhibition of Sema3 A expression or accumulation.

In another embodiment, the neuroprotection is through inhibition or prevention of neuron apoptosis.

In another embodiment, the neuroprotection is through anti-inflammatory effect for protecting neurons against cellular stresses.

In another embodiment, the neuroprotection is through reduction of overproduction of NO.

In a further embodiment, the miRNA stated in the invention is used as free radical scavenger or anti-inflammatory drug.

In another further embodiment, the neuroprotection is associated with neuronal or brain injury or neurodegenerative diseases.

DETAILED DESCRIPTION OF THE INVENTION

Figure 1:
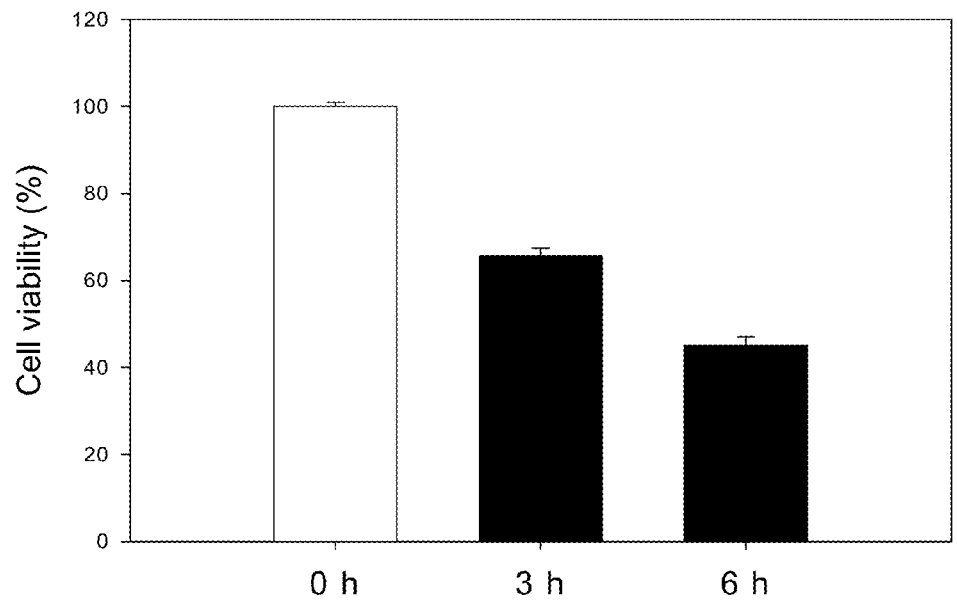
FIG. 1 shows a decrease of cell viability by 3-hr and 6-hr oxygen and glucose deprivation (OGD) (A panel) and a decrease of endogenous MiR-195 (B panel) in OGD-induced SH-S5Y5 cells.
Figure 1:
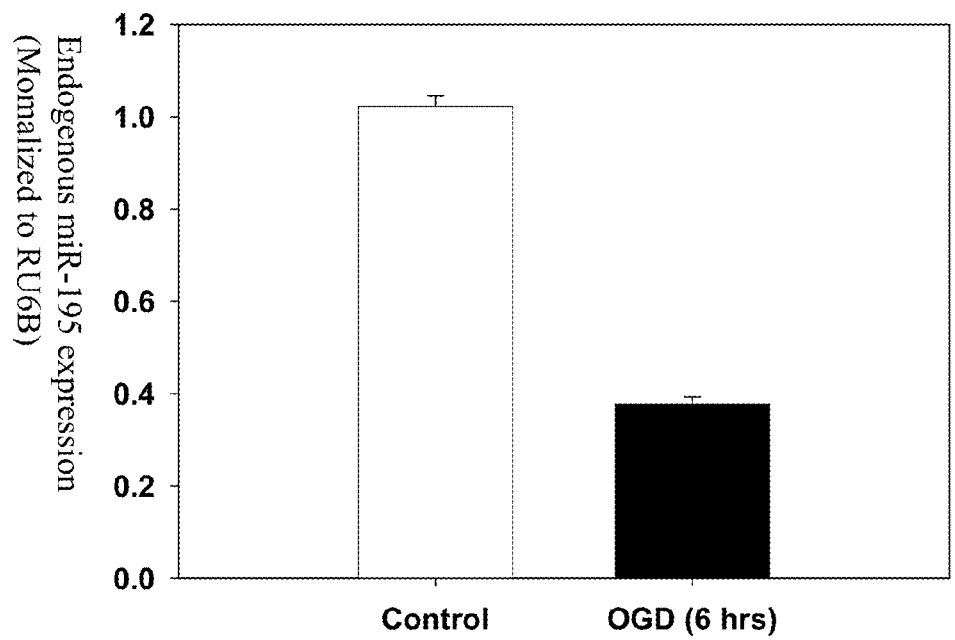

The invention surprisingly found that increase of microRNA-195 can provide neuroprotection.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference from what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

The terms "a" and "an" refer to one or more than one (i.e., at least one) of the grammatical object of the article.

As used herein, the term "or" in the claims refers to "and/or" unless explicitly indicated to refer to alternatives only or unless the alternatives are mutually exclusive.

The term "treat," "treatment" or "treating" means reducing the frequency, extent, severity and/or duration with which symptoms of neuron or nervous system damage are experienced by a patient.

The term "prevent," "prevention" or "preventing" means decreasing possibility of incurring neuron or nervous system diseases.

As used herein, the term "subject" refers to any recipient of a treatment using a microRNA or microRNA mimic or a treatment given for a similar purpose as described herein.

The term miRNA, miR and microRNA can be used interchangeable and refers to 21-23 nt non-coding RNAs derived from endogenous genes that act as post-transcriptional regulators of gene expression. They are processed from longer (ca 70-80 nt) hairpin-like precursors termed pre-miRNAs by the RNAse III enzyme Dicer. MiRNAs assemble in ribonucleoprotein complexes termed miRNPs and recognise their target sites by antisense complementarity thereby mediating down-regulation of their target genes. Near-perfect or perfect complementarity between the miRNA and its target site results in target mRNA cleavage, whereas limited complementarity between the miRNA and the target site results in translational inhibition of the target gene. As used herein interchangeably, a "miR gene product," "microRNA," "miR," "miR" or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., $E.$ $coli$ RNAse III)) into an active 21-23 nucleotide RNA molecule. This active 21-23 nucleotide RNA molecule is also called the "processed" miR gene transcript or "mature" miRNA.

Pri-miRNA Refers to the primary miRNA transcript. Initially, miRNA genes are transcribed by RNA polymerase II into long primary miRNAs (pri-miRNAs). The processing of these pri-miRNAs into the final mature miRNAs occurs stepwise and compartmentalized. In animals, pri-miRNAs are processed in the nucleus into 70-80 nucleotide precursor miRNAs (pre-miRNAs) by the RNase III enzyme Drosha.

The term "miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA. Pre-miRNA" or "pre-miR" means a non-coding RNA having a hairpin structure, which contains a miRNA. In certain embodiments, a pre-miRNA is the product of cleavage of a pri-miR by the double-stranded RNA-specific ribonuclease known as Drosha.

The term "effective amount" means an amount of miRNAs or its mimic effective to inhibit and/or treat and/or prevent neuron or nervous system damage. For example, the effective amount of the miRNAs may inhibit neuron or nervous system damage and/or relieve to some extent one or more of the symptoms associated with the disorder caused by neuron or nervous system damage.

In one aspect, the invention provides a method for providing neuroprotection comprising administering to a subject an effective amount of a microRNA selected from a miRNA-195, a modified miRNA-195 and a combination thereof.

According to the invention, the miRNA described herein refers to miRNA-195 or a modified microRNA thereof or a combination thereof.

In one embodiment, at least one modified moiety comprises a base bonded to an amino acid residue as the backbone unit. Modified moieties that have at least one base bonded to an amino acid residue will be referred to herein as peptide nucleic acid (PNA) moieties. Such moieties are nuclease resistance, and are known in the art. Molecules having PNA moieties are generally referred to as peptide nucleic acids (Nielson, Methods Enzymol. 313, 156-164 (1999); Elayadi, et al, id.; Braasch et al., Biochemistry 41, 4503-4509 (2002), Nielsen et al., Science 254, 1497-1500 (1991)).

The modified miRNA-195 includes, but not limited to, a pre-miRNA-195 or all pyrimidine nucleotides in miRNA are replaced by their 2'-O-methyl analogs to improve miRAN stability) or a mimic of a miRNA-195 (for example, a synthetic miRNA-195 duplex).

In one embodiment, the design of miR-195 mimics useful in this invention, and in particular, the choice of target sequences for miR-195 mimics can be based on one existing RNA species that can be cleaved inside a cell to form miR-195, with compatible modifications described herein. Modified shRNAs include molecules containing nucleotide analogues, including those molecules having additions, deletions, and/or substitutions in the nucleobase, sugar, or backbone; and molecules that are cross-linked or otherwise chemically modified. The modified nucleotide(s) may be within portions of the miR-195 molecule, or throughout it. For instance, the miR-195 molecule may be modified, or contain modified nucleic acids in regions at its 5' end, its 3' end, or both, and/or within the guide strand, passenger strand, or both, and/or within nucleotides that overhang the 5' end, the 3' end, or both.

In one embodiment, the miRNA-195 may comprise an original human miRNA-195 (the sequence of the original human miRNA-195 is UAGCAGCACAGAAAUAUUGGC; SEQ ID NO:1), a modified human miRNA-195, for example, a human pre-miRNA-195 (the sequence of the human pre-miRNA-195 is AGCUUCCCUGGCUCUAGCAGCACA-GAAAUAUUGGCACAGGGAAGCGAGUCUG CCAAUAUUGGCUGUGCUGCUCCAG-GCAGGGUGGUG; SEQ ID NO:2) or a mimic of a human miRNA-195.

In one embodiment, the modified single stranded microRNA molecule can be any of the microRNA molecules, hairpin precursor molecules, or equivalents thereof described above, except that the modified molecule comprises at least one modified moiety (i.e., at least one moiety is not an unmodified deoxyribonucleotide moiety or an unmodified ribonucleotide moiety). In this embodiment, the modified microRNA molecule comprises a minimum number of ten moieties, preferably a minimum of thirteen, more preferably a minimum of fifteen, even more preferably a minimum of eighteen, and most preferably a minimum of twenty-one moieties.

The modified microRNA molecules preferably comprise a maximum number of fifty moieties, more preferably a maximum of forty, even more preferably a maximum of thirty, most preferably a maximum of twenty-five, and optimally a maximum of twenty-three moieties. A suitable range of minimum and maximum numbers of moieties may be obtained by combining any of the above minima with any of the above maxima.

Each modified moiety comprises a base bonded to a backbone unit. The backbone unit may be any molecular unit that is able to stably bind to a base and to form an oligomeric chain. In this specification, the backbone units of a modified moiety do not include the backbone units commonly found in naturally occurring DNA or RNA molecules.

Such modified microRNA molecules have increased nuclease resistance. Therefore, the nuclease resistance of the molecule is increased compared to a sequence containing only unmodified ribonucleotide moieties, unmodified deoxyribonucleotide moieties or both. Such modified moieties are well known in the art, and were reviewed, for example, by Kurreck, Eur. J. Biochem. 270, 1628-1644 (2003).

A modified moiety can occur at any position in the microRNA molecule. For example, to protect microRNA molecules against 3'→5' exonucleases, the molecules can have at least one modified moiety at the 3' end of the molecule and preferably at least two modified moieties at the 3' end. If it is desirable to protect the molecule against 5'→3' exonuclease, the microRNA molecules can have at least one modified moiety and preferably at least two modified moieties at the 5' end of the molecule. The microRNA molecules can also have at least one and preferably at least two modified moieties between the 5' and 3' end of the molecule to increase resistance of the molecule to endonucleases. Preferably, at least about 10%, more preferably at least about 25%, even more preferably at least about 50%, and further more preferably at least about 75%, and most preferably at least about 95% of the moieties are modified. In one embodiment, all of the moieties are modified (e.g., nuclease resistant).

In one example of a modified microRNA molecule, the molecule comprises at least one modified deoxyribonucleotide moiety. Suitable modified deoxyribonucleotide moieties are known in the art. Such modified deoxyribonucleotide moieties comprise, for example, phosphorothioate deoxyribose groups as the backbone unit. Another suitable example of a modified deoxyribonucleotide moiety is an N'3-N'5 phosphoroamidate deoxyribonucleotide moiety, which comprises an N'3-N'5 phosphoroamidate deoxyribose group as the backbone unit.

A suitable example of a modified ribonucleotide moiety is a ribonucleotide that has a methylene bridge between the 2'-oxygen atom and the 4'-carbon atom. An oligoribonucleotide molecule comprising ribonucleotide moieties that has a methylene bridge between the 2'-oxygen atom and the 4'-carbon atom is generally referred to as locked nucleic acid (LNA). See, for example, Kurreck et al., Nucleic Acids Res. 30, 1911-1918 (2002); Elayadi et al., Curr. Opinion Invest. Drugs 2, 558-561 (2001); Orum et al., Curr. Opinion Mol. Ther. 3, 239-243 (2001); Koshkin et al., Tetrahedron 54, 3607-3630 (1998); Obika et al., Tetrahedron Lett. 39, 5401-5404 (1998). Locked nucleic acids are commercially available from Proligo (Paris, France and Boulder, Colo., USA.). The mir-RNAs and their mimics in the present invention can be a "LNA-modified oligomer", which containing at least one or more LNA monomer. In some embodiment, the LNA-modified miR-195 sequences include but not limited to the following sequences. The LNA-modified nucleotides are underlined in the following sequences.

```
                                            (SEQ ID NO: 3)
        miR-195 LNA 1:  UAGCAGCACAGAAAUAUUGGC (SEQ ID NO: 4)
        miR-195 LNA 2:  TAGCAGCACAGAAAUAUUGGC (SEQ ID NO: 5)
        miR-195 LNA 3:  TAGCAGCACAGAAATATTGGC (SEQ ID NO: 6)
        miR-195 LNA 4:  TAGCAGCACAGAAATATTGGC (SEQ ID NO: 7)
        miR-195 LNA 5:  TAGCAGCACAGAAATATTGGC
```

In another embodiment, miRNA can be combined with a nanoparticle. Accordingly, the invention provides a pharmaceutical mixture comprising a miRNA or a modified miRNA thereof combined with a nanoparticle. Preferably, the nanoparticles are liposomes, micelles, metal nanoparticles, or polymeric nanoparticles. Nanoparticles are defined as particulate dispersions or solid particles with a size in the range of 10-1000 nm. Nanoparticles can be prepared from a variety of materials such as lipids, proteins, polysaccharides and synthetic polymers. Depending upon the method of preparation, nanoparticles, nanospheres or nanocapsules can be obtained. Nanocapsules are systems in which the agent is confined to a cavity surrounded by a unique polymer membrane, while nanospheres are matrix systems in which the drug is physically and uniformly dispersed. Nanoparticles have been prepared most frequency by three methods: (1) dispersion of preformed polymers; (2) polymerization of monomers; and (3) ionic gelation or coacervation of hydrophilic polymers. However, other methods such as supercritical fluid technology and particle replication in non-wetting templates (PRINT) have also been described in the literature for production of nanoparticles.

The miRNA molecule of the invention can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the miRNA molecule can also be produced directly by biological or chemical synthesis, without having to be processed from the miR precursor. When a miRNA is referred to herein by name, the name corresponds to both the precursor and mature forms, unless otherwise indicated.

Micro RNAs can be generated in vivo from pre-miRNAs by enzymes called Dicer and Drosha that specifically process long pre-miRNA into functional miRNA. The miRNAs or precursor miRNAs featured in the invention can be synthesized in vivo by a cell-based system or can be chemically synthesized. MiRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. Methods of synthesis and chemical modifications are described in greater detail below.

A miRNA or a pre-miRNA can be designed and synthesized to include a region of noncomplementarity (e.g., a region that is 3, 4, 5, or 6 nucleotides long) flanked by regions of sufficient complementarity to form a duplex (e.g., regions that are 7, 8, 9, 10, or 11 nucleotides long). For increased nuclease resistance and/or binding affinity to the target, the miRNA sequences can include 2'-O-methyl, 2'-fluorine, 2'-O-methoxyethyl, 2'-O-aminopropyl, 2'-amino, and/or phosphorothioate linkages. The inclusion of furanose sugars in the oligonucleotide backbone can also decrease endonucleolytic cleavage. A miRNA or a pre-miRNA can be further modified by including a 3'-cationic group, or by inverting the nucleoside at the 3'-terminus with a 3'-3' linkage. In another alternative, the 3'-terminus can be blocked with an aminoalkyl group, e.g., a 3'-CS-aminoalkyl dT. Other 3'-conjugates can inhibit 3'-5' exonucleolytic cleavage.

In one embodiment, a miRNA or a pre-miRNA includes a modification that improves targeting, e.g. a targeting modification described above. Examples of modifications that target miRNA molecules to particular cell types include carbohydrate sugars such as galactose, N-acetylgalactosamine, mannose; vitamins such as folates; other ligands such as RGDs and RGD mimics; and small molecules or other known protein-binding molecules.

A miRNA or a pre-miRNA can be constructed using chemical synthesis and/or enzymatic ligation reactions using procedures known in the art. For example, a miRNA or a pre-miRNA can be chemically synthesized using naturally occurring nucleotides or variously modified nucleotides designed to increase the biological stability of the molecules or to increase the physical stability of the duplex formed between the miRNA or a pre-miRNA and target nucleic acids, e.g., phosphorothioate derivatives and acridine substituted nucleotides can be used. Other appropriate nucleic acid modifications are described herein. Alternatively, the miRNA or pre-miRNA nucleic acid can be produced biologically using an expression vector into which a nucleic acid has been subcloned in an antisense orientation, i.e., RNA transcribed from the inserted nucleic acid will be of an antisense orientation to a target nucleic acid of interest.

According to the invention, miRNA or a modification thereof is useful in providing neuroprotection that refers to the ability to prevent or reduce death or damage to nerve cells, including neurons and glia, or rescuing, resuscitating or reviving nerve cells, e.g., following in pathological or harmful conditions to the brain, central nervous system or peripheral nervous system. Neuroprotection includes the regeneration of nerve cells, i.e. the re-growth of a population of nerve cells after disease or trauma. Neuroprotection is the mechanisms and strategies used to protect against brain/neuronal injury or degeneration in the nervous system following acute disorders (e.g. stroke or brain or nervous system injury/trauma, hypoxia, spinal cord injury or peripheral nerve injury) or as a result of chronic neurodegenerative diseases (e.g. Parkinson's disease, Alzheimer's disease, multiple sclerosis). The goal of neuroprotection is to limit neuronal dysfunction/death after the nervous system injury and attempt to maintain the highest possible integrity of cellular interactions in the brain resulting in an undisturbed neural function. By providing neuroprotection, miRNA or a variant thereof can be used to treat neuronal injury (such as stroke, particularly ischemic stroke, brain injury, hypoxia, spinal cord injury or peripheral nerve injury) and treat/or prevent neurodegenerative diseases. As such, in one embodiment, the present invention relates to the use of micro-RNA as active ingredient in the manufacture of a medicament for the regeneration of nerve cells. In other words, the present invention relates to micro-RNAs for use for the protection and/or regeneration of nerve cells. Similarly, the present invention relates to a method of protection and/or regenerating nerve cells comprising administering to a subject in need thereof an effective amount of micro-RNAs or the mimics.

Neuroprotection may be determined directly by, for example, measuring the delay or prevention of neuronal death, such as, for example, by a reduction in the number of apoptotic neurons in cerebrocortical cultures following a stress. Neuroprotection may also be determined directly by, for example, measuring the severity or extent of damage to, or functional loss by, a tissue or organ of the nervous system following such a stress, such as, for example, by measuring a decrease in the size of brain infarcts after occlusion of the middle cerebral artery (MCAO) or reperfusion injury. Also, neuroprotection can be identified by magnetic resonance imaging (measuring brain volume, tractography, levels of N-acetyl-asparte by spectroscopy) or by retinal imaging with optic coherent imaging (retinal nerve fiber layer thining) or retinal spectroscopy (levels of cytochrome c, oxyhemoglobin, lactate, glutamate, iNOS). Alternatively, neuroprotection may be determined indirectly by detecting the activation of one or more biological mechanisms for protecting neurons, including, but not limited to, detecting activation of the Sema3 pathway or reducing the overproduction of NO generated via iNOS in neuron to stop the neuronal cell death.

According to the invention, the miRNA-195 has the sequence as shown in SEQ ID NO: 1 or SEQ ID NO: 2. In another embodiment, miRNA or a variant thereof combined with a nanoparticle. Preferably, the nanoparticles are liposomes, micelles, metal nanoparticles, or polymeric nanoparticles.

In a particular embodiment, liposomes are used to deliver a miRNA product to a subject. Liposomes can also increase the blood half-life of nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in U.S. Pat. Nos. 4,235,871, 4,501,728, 4,837,028, and 5,019,369, the entire disclosures of which are incorporated herein by reference.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53.

The liposomes for use in the present methods can comprise a ligand molecule that targets the liposome to target cells. The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Consequently, the invention found that miRNA-195 has several beneficial effects and functions in proving neuroprotection so that miRNA-195 can be used to treat neuronal or brain injury and treat/or prevent neurodegenerative diseases including acute or chronic neurodegenerative diseases.

The term "neurodegenerative disease" is used herein also to describe an acute, progressive or chronic disease which is caused by damage to the central nervous system and which damage can be reduced and/or alleviated through the microRNAs treatment according to the present invention directly into, but preferably via systemic route that will allow the cells or their soluble factors to reach the damaged areas of the brain and/or spinal cord of the patient. The term "acute neurodegenerative disease" means and disease or disorder associated with an abrupt insult, resulting in associated neuronal death or compromise. Exemplary acute neurodegenerative diseases include cerebrovascular insufficiency, focal or diffuse brain trauma, spinal cord injury, cerebral ischemia or infarction, including emolic occlusion and thrombotic occlusion, perinatal hypoxic-ischemia, neonatal hypoxia-ischaemic encephalopathy, perinatal asphyxia, cardiac arrest, intracranial hemorrhage, subarachnoid hemorrhage, stroke, and traumatic brain injury. In one embodiment, the neurodegenerative disease is intracranial hemorrhage or subarachnoid hemorrhage. Subarachnoid hemorrhage (SAH) means blood entering into the subarachnoid space—the area between the arachnoid membrane and the pia mater surrounding the brain. This may occur spontaneously, usually from a ruptured cerebral aneurysm, or may result from head injury. Symptoms of SAH include a severe headache with a rapid onset, vomiting, confusion or a lowered level of consciousness, and sometimes seizures. The diagnosis is generally confirmed with a CT scan of the head, or occasionally by lumbar puncture. Treatment is by prompt neurosurgery or radiologically guided interventions with medications and other treatments to help prevent recurrence of the bleeding and complications. SAH is a medical emergency and can lead to death or severe disability—even when recognized and treated at an early stage. Patients survives SAH often have neurological or cognitive impairment.

Exemplary neurodegenerative diseases which may be treated using the methods according to the present invention include for example, Parkinson's disease, Huntington's disease, amyotrophic lateral sclerosis, Alzheimer's disease, Rett Syndrome, lysosomal storage diseases ("white matter disease" or glial demyelination disease, as described, for example by Folkerth, J. Neuropath. Exp. Neuro., September 1999, 58:9), including Sanfillippo, Gaucher disease, Tay Sachs disease (beta hexosaminidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of said patient or which has occurred from physical injury to the brain and/or spinal cord. Neurodegenerative diseases also include neurodevelopmental disorders including for example, cerebral palsy, autism and related neurological diseases such as schizophrenia, among numerous others.

The present invention further provides a method for the prevention or treatment of neuron degenerative disease, such as Alzheimer's dementia (AD) or Parkinson disease (PD), which method comprises providing the mir-RNAs, mir-195 mimics, to inhibit the Sema3A expression, accumulation or activity in a subject or patient.

The method for the prevention or treatment of AD or PD comprises administering to a patient in need of such treatment an effective amount or a substance of the mi-RNAs that inhibits Sema3 A expression, accumulation or activity.

A "subject" or "patient" is a human or an animal likely to develop AD or PD, more particularly a mammal, preferably a human, rodent or primate, as described above in connection with diagnostic applications. The term "prevention" refers to the prevention of the onset of AD or PD, which means to prophylactically interfere with a pathological mechanism that results in the disease. In the context of the present invention, such a pathological mechanism can be an increase of Sema3 A expression, or accumulation. The patient may be a subject that has an increased risk of developing the disease. For example, for AD, such subject may have a genetic predisposition to developing an amyloidosis, such as a person from a family that has members with familial AD (FAD). Alternatively, someone in his or her seventh or eighth decade is at greater risk for age-related AD The term "therapeutically effective amount" is used herein to mean an amount or dose sufficient of miRNAs, e.g. mir-195, to decrease the level of Sema3A activity e.g., by about 10%, preferably by about 50%), and more preferably by about 90%>percent. Preferably, a therapeutically effective amount can ameliorate or present a clinically significant deficit in the activity, function and effects of Sema3A. Alternatively, a therapeutically effective amount of miRNAs, e.g. mir-195, is sufficient to cause an improvement in a clinically significant condition in the subject to which it is administered.

The inhibitory activity of mir-195 can directly against the Sema3A by other intracellular signaling partner, CDC42, and its downstream effectors, such as upregulated BCL2 and downregulated Caspase 3 to prevent the neuron apoptosis.

In one embodiment, the miRNAs in the present invention demonstrates the protection of the largest population of non-excitable astrocyte cells in mammalian CNS by displaying the anti-inflammatory property for protecting neurons against a variety of cellular stresses, such as excitotoxicity and oxidative stress, etc., spinal cord damage, ataxia and alcoholism.

In a further experiment regarding the activated astrocytes mediated neuronal cell death, the miRNAs of the current invention reduce the overproduction of NO generated via iNOS in neuron to stop the neuronal cell death.

The miRNAs of this invention are potent free radical scavengers and anti-inflammatory drugs by leveraging the imbalance between generation of reactive oxygen species and the activity of the anti-oxidant, which is termed oxidative stress and demonstrating the attenuated activities in the LPS-induced iNOS expression test. Therefore, the miRNAs of this invention relieve the hypoxic injury that resulted from the neuron damage and implicate in a wide variety of human degenerative disorders of the CNS, including Alzheimer's disease, Parkinson disease, and in pathological conditions such as ischemia.

The miRNAs in the current invention further direct to the treatment of any suitable ischemia. Ischemia, as used herein, is a reduced blood flow to an organ(s) and/or tissue(s). The reduced blood flow may be caused by any suitable mechanism including a partial or complete blockage (an obstruction), a narrowing (a constriction), and/or a leak/rupture, among others, of one or more blood vessels that supply blood to the organ(s) and/or tissue(s). Accordingly, ischemia may be created by thrombosis, an embolism, atherosclerosis, hypertension, hemorrhage, an aneurysm, surgery, trauma, medication, and/or the like. The reduced blood flow thus may be chronic, transient, acute, sporadic, and/or the like.

In a further object of the current invention provide the treatment of stroke. Stroke, as used herein, is brain ischemia produced by a reduced blood supply to a part (or all) of the brain. Symptoms produced by stroke may be sudden (such as loss of consciousness) or may have a gradual onset over hours or days. Furthermore, the stroke may be a major ischemic attack (a full stroke) or a more minor, transient ischemic attack, among others. Symptoms produced by stroke may include, for example, hemiparesis, hemiplegia, one-sided numbness, one-sided weakness, one-sided paralysis, temporary limb weakness, limb tingling, confusion, trouble speaking, trouble understanding speech, trouble seeing in one or both eyes, dim vision, loss of vision, trouble walking, dizziness, a tendency to fall, loss of coordination, sudden severe headache, noisy breathing, and/or loss of consciousness. Alternatively, or in addition, the symptoms may be detectable more readily or only via tests and/or instruments, for example, an ischemia blood test (e.g., to test for altered albumin, particular protein isoforms, damaged proteins, etc.), an electrocardiogram, an electroencephalogram, an exercise stress test, and/or the like.

The miRNAs of the current invention provide treatment of ischemic subjects to reduce ischemic injury to the subjects. An ischemic subject, as used herein, is any person (a human subject) or animal (an animal subject) that has ischemia, an ischemia-related condition, a history of ischemia, and/or a significant chance of developing ischemia after treatment begins and during a time period in which the treatment is still effective.

Ischemic subjects for treatment may be selected by any suitable criteria. Exemplary criteria may include any detectable symptoms of ischemia, a history of ischemia, an event that increases the risk of (or induces) ischemia (such as a surgical procedure, trauma, administration of a medication, etc.), and/or the like. A history of ischemia may involve one or more prior ischemic episodes. In some examples, a subject selected for treatment may have had an onset of ischemia that occurred at least about one, two, or three hours before treatment begins, or a plurality of ischemic episodes (such as transient ischemic attacks) that occurred less than about one day, twelve hours, or six hours prior to initiation of treatment.

One skilled in the art can readily determine an effective amount of a miRNA product to be administered to a given subject, by taking into account factors, such as the size and weight of the subject; the extent of disease penetration; the age, health and sex of the subject; the route of administration; and whether the administration is regional or systemic. For example, an effective amount of an isolated miRNA product can be based on the approximate weight of a subject to be administered. An effective amount of the isolated miRNA product based on the weight of a subject can be in the range from about 1.0 nanomole/kg to about 15.0 nanomole/kg. Preferably, the amount is about 3.0 to about 10.0 nanomole/kg or about 3.0 to about 7.0 nanomole/kg. More preferably, the amount is about 3.3 to about 6.6 nanomole/kg.

One skilled in the art can also readily determine an appropriate dosage regimen for the administration of an isolated miRNA product to a given subject. For example, a miRNA product can be administered to the subject once or twice. Where a dosage regimen comprises multiple administrations, it is understood that the effective amount of the miRNA product administered to the subject can comprise the total amount of the product administered over the entire dosage regimen.

A miRNA can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., intra-muscular injection, peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the target.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

EXAMPLE

Example 1

Neuroprotection Assay for MiR-195

Figure 2:
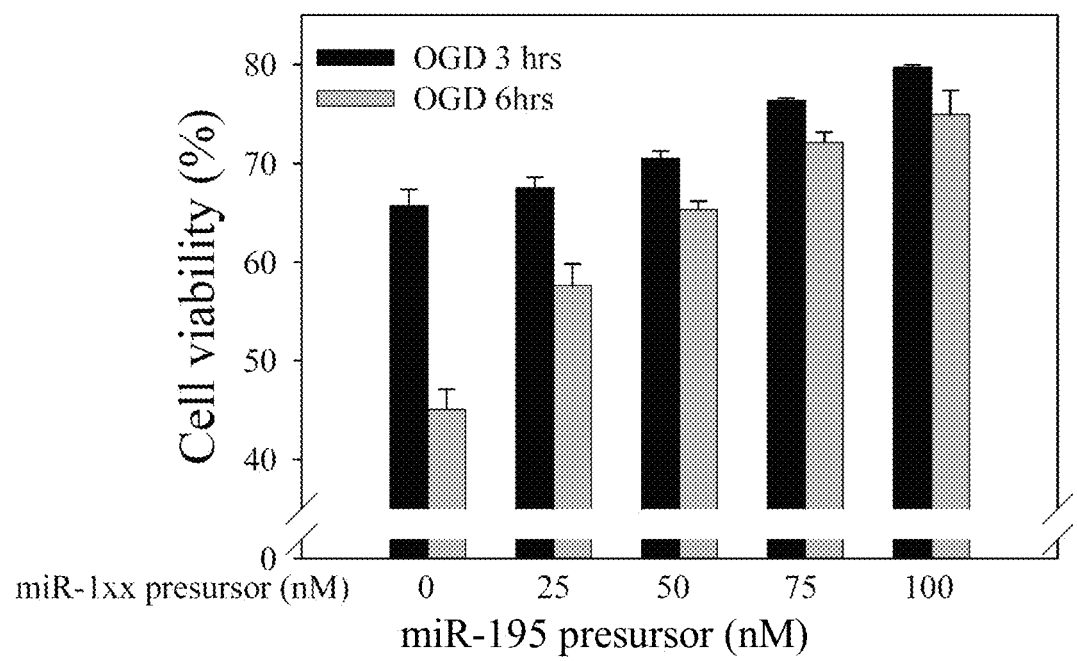
FIG. 2 shows the effect of miR-195 on increasing cell survival after 3-hr and 6-hr OGD. Cell survival was measured at $24^{th}$ hours.

The neuroprotecive effect of miR-195 in oxygen-glucose deprivation (OGD) in the neuroblastoma cell line (SH-SY5Y) was tested as an in vitro model for neuronal injury. The endogenous expression of miR-195 was significantly decreased (62%) at 6 h of OGD (see FIG. 1B) and SH-SY5Y cell viability was reduced by 35% after 3-h OGD and 55% after 6-h of OGD as compared to the control group (see FIG. 1A). To determine the role of miR-195 in the protective effect of SH-SY5Y under OGD, miR-195 mimic was transfected into the cell using Lipofectamine 2000 reagent (Invitrogen, Calif., USA). The degree of miR-195-induced cell viability was assessed by dimethyl-thiazol-diphenyltetrazoliumbromide (MTT; Sigma-Aldrich, Mo., USA). The therapeutic effect of miR-195 mimic (concentrations between 25-100 nM) on cell viability at 3 and 6 h of OGD is shown in FIG. 2. As seen in FIG. 2, miR-195 had a dose-dependent effect on rescuing the damage cells. Therefore, the in vitro study showed a potential of miR-195 in neuroprotection.

Figure 3:
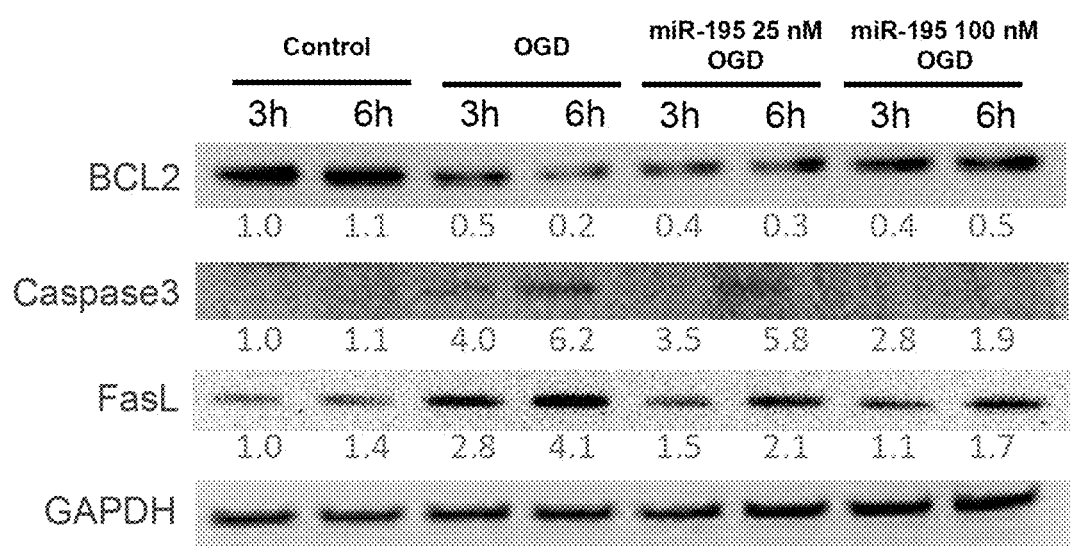
FIG. 3 shows miR-195 influences the expression of several genes involved in the apoptosis pathway. miR-195 increases the anti-apoptotic gene (BCL2) expression but inhibits two apoptotic genes (Caspase3 and FasL). In addition, miR-195 has a dose-dependent effects on these genes.

To investigate the impacts of miR-195 on the apoptosis signal pathway, the changes of B-cell lymphoma 2 (Bcl-2), Fas ligand (FasL) and caspase-3 protein levels in the OGD-induced SH-SY5Y cell death were also assessed by western blot. It was found that miR-195 treatment increased the protein level of Bcl-2, an anti-apoptotic factor, in SH-SY5Y. MiR-195 treatment also substantially reduced the protein levels of apoptotic factors FasL and caspase3 (FIG. 3).

Figure 4:
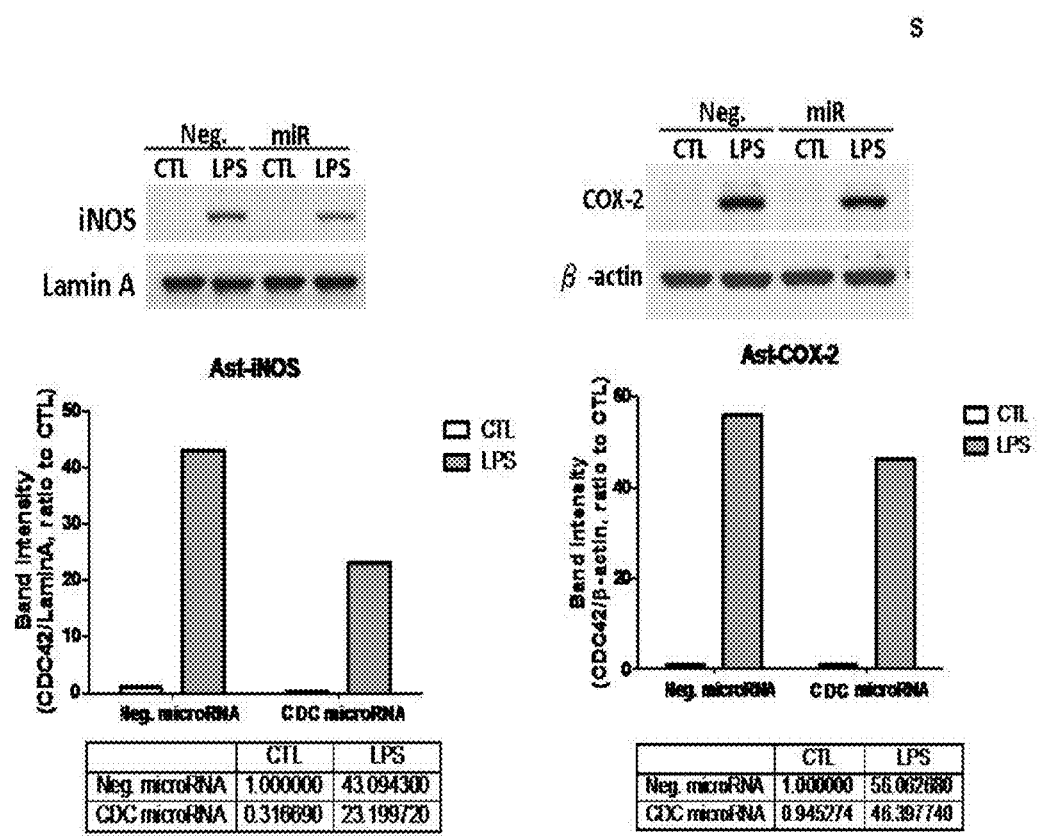
FIG. 4 shows effect of miRNA-195 on the LPS-induced proinflammatory response in astrocytes.

Lipopolysaccharide (LPS)-induced astrogliosis: LPS stimulation of primary cultured astrocytes is a well accepted in vitro model to mimic astrocyte reactivation during brain injuries, including stroke. Inducible nitric oxide synthase (iNOS) in astrocytes contributes inflammation in brain. iNOS can be de novo induced after ischemic stroke. Inhibition of iNOS activity or iNOS gene deletion in rodent models of ischemic stroke provides neuroprotection. COX-2 is induced in response to ischemic and COX-2 is neuroexcitotoxic following brain injuries. To investigate miR-195 effect on primary astrocytes, mice were anesthetized and then decapitated. The cerebral cortex was carefully removed and homogenized. The cells suspension was diluted and the cells were seeded on flasks. Microglia and oligodendrocytes were removed by orbital shaking the flask. The suspended cells were decanted to obtain a pure astrocyte layer adhering to the bottom. The purified astrocytes were subcultured and then treated with LPS for 1 hour. Real-time PCR was used to measure the mRNA levels of inducible nitric-oxide synthase (iNOS) and COX-2. Western blotting was used to measure the protein expression of iNOS and COX-2 (see FIG. 4). It was found that miR-195 can reduce harmful iNOS and COX-2 to exert neuroprotective effects in astrocytes.

Figure 5:
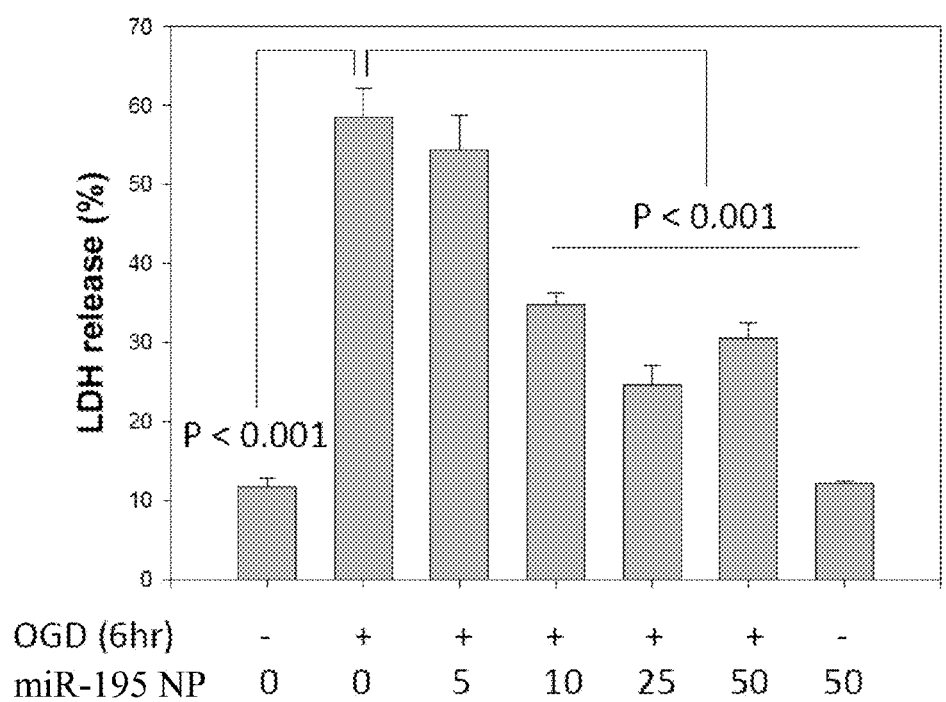
FIG. 5 shows miR-195 carried by nanoparticle (NP) has a dose-dependent effect to prevent cell death after OGD.

Subsequently, we used nanoparticle carrying miR-195 (NP-miR-195) to repeat the same OGD cellular study. At 6 h of OGD, the profile of cell death was analyzed by Cytotoxicity Detection Kit (lactose dehydrogenase, LDH; Roche). OGD for 6 hours strongly promoted LDH secretion by 47% over the basal level. However, LDH was effectively suppressed by 49% in the presence of NP-miR-195 (25 nM; FIG. 5).

Figure 6:
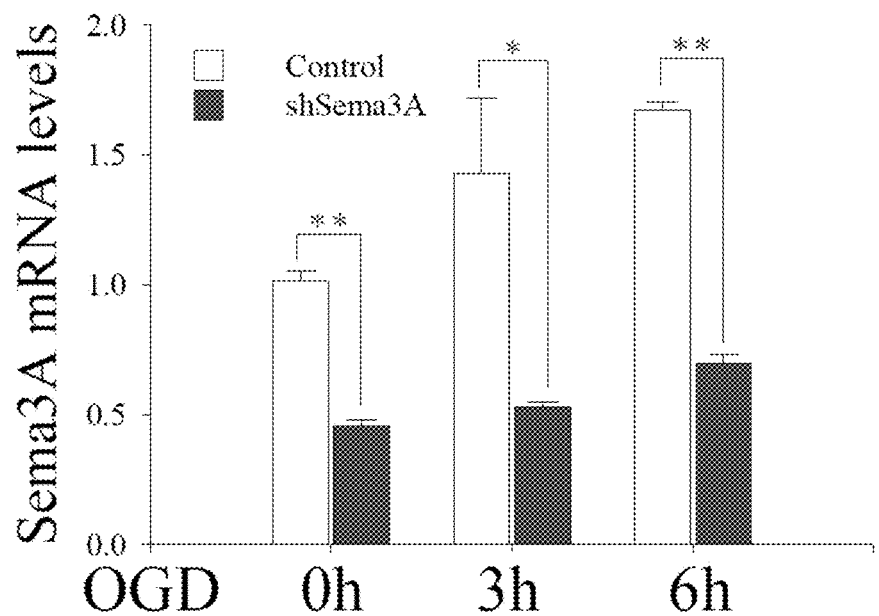
FIG. 6 shows the knockdown of Sema3A and Cdc42 enhances SH-S5Y5 cell viability.
Figure 6:
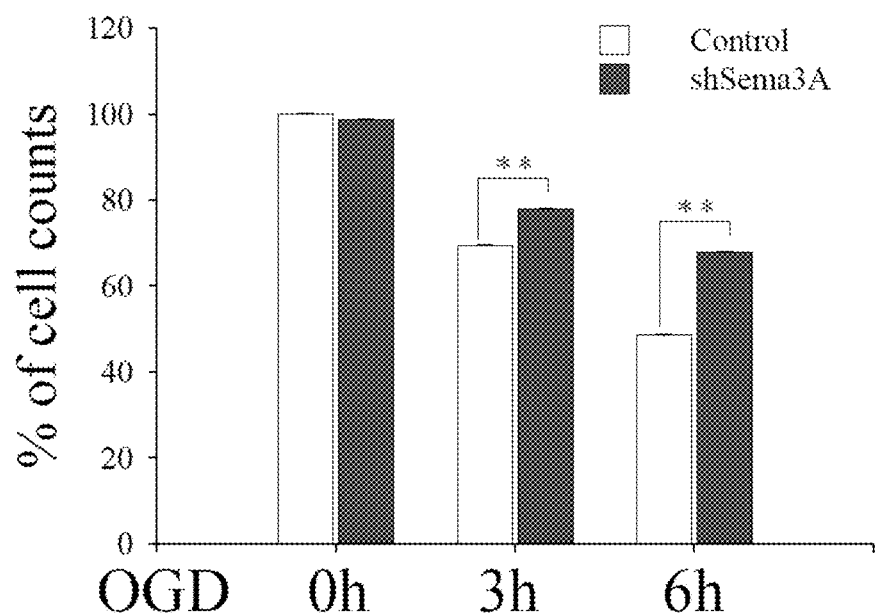
Figure 6:
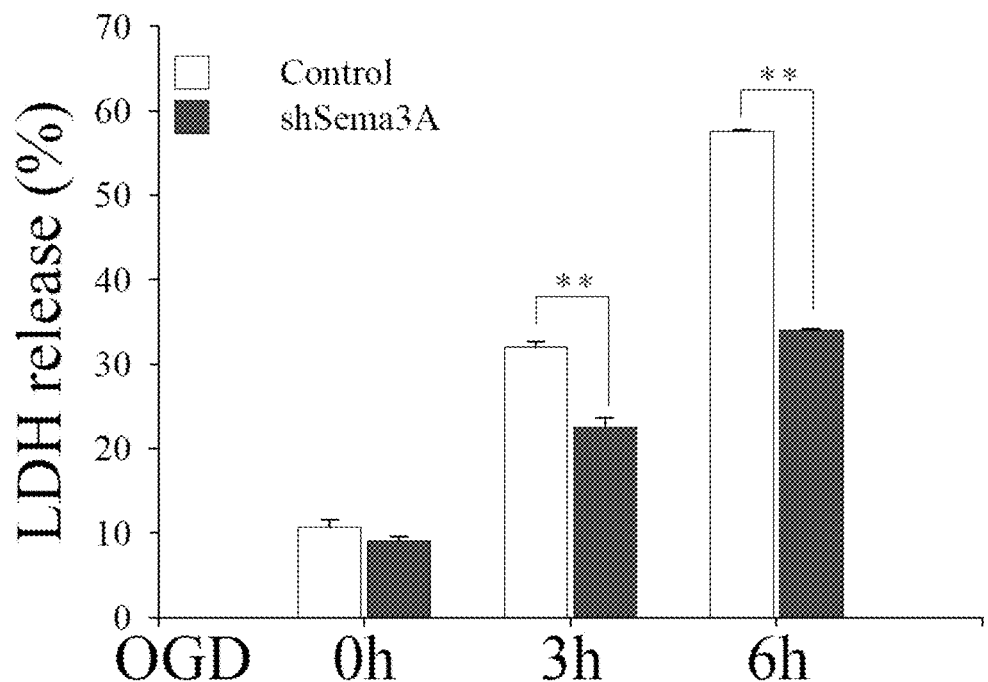
Figure 6:
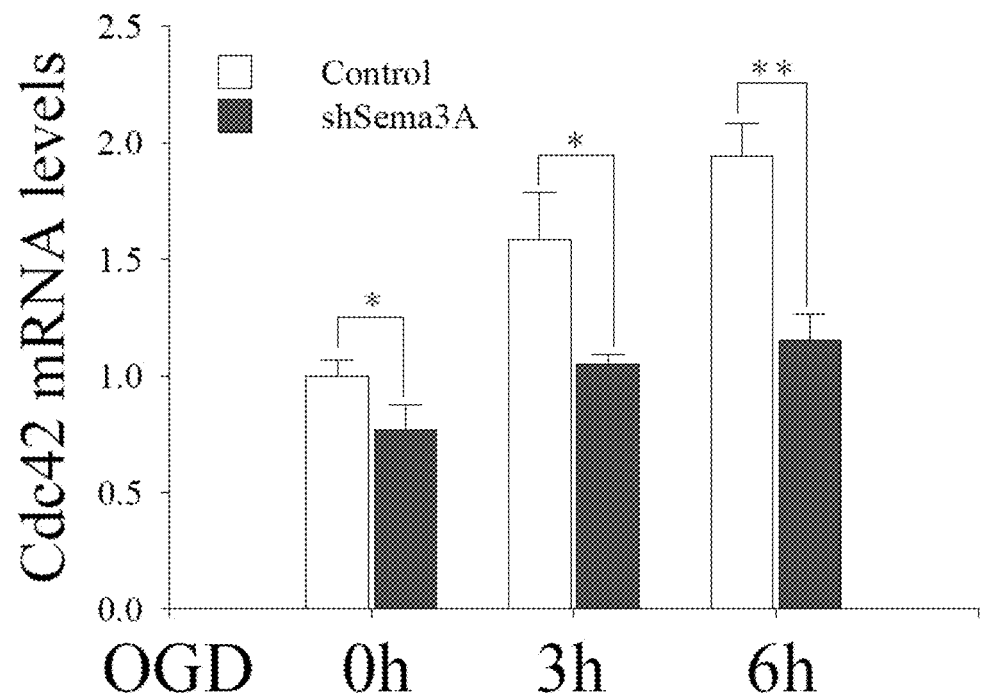
Figure 7:
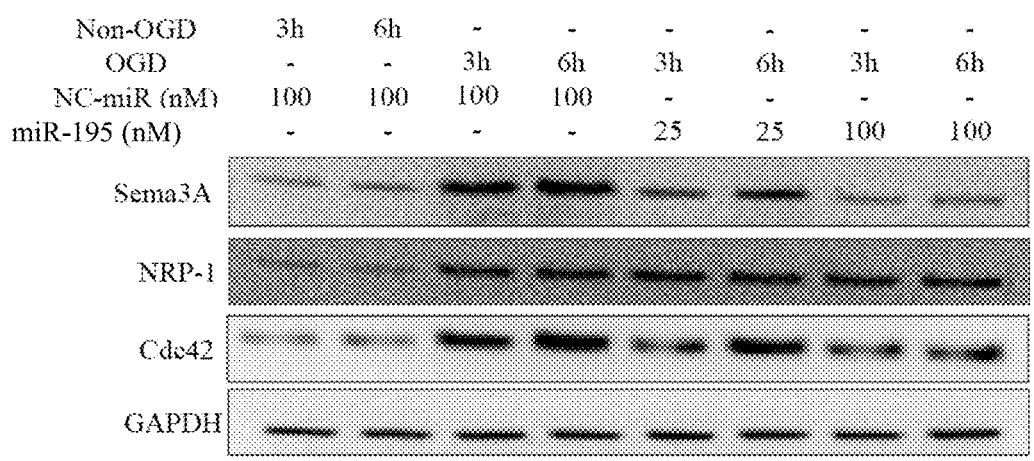
FIG. 7 shows MiR-195 has dose-dependent effect on regulating Sema3A and Cdc42 at the protein levels.

Furthermore, shRNA targeting Sema3A (shSema3A) was used to knockdown Sema3A and the downstreamed Cdc42 to prove that the cell viability is increased. The results show that the knockdown of Sema3A enhanced SH-S5Y5 cell viability (see FIG. 6). In FIG. 6, (A) The change of Sema3A mRNA level was determined by quantitative real-time PCR. (B and C) OGD-treated cells viability was measured by cell counts and LDH release. (D) shSema3A knocked down Cdc42 mRNA in 3 h and 6 h OGD-treated cells as determined by quantitative real-time PCR. Data are means±SD from three experiments; *$P<0.05$, and **$P<0.01$ vs. control cells not exposed to OGD. Scrambled shRNA was used as transfection control. 3 h or 6 h OGD-treated Sh-S5Y5 cells were transfected with the miR-195 mimic or NC-miR. Sema3A, Cdc42 and Nrp-1 protein levels in cells were detected by western blot at 24 h incubation. FIG. 7 shows that MiR-195 regulates Sema3A and Cdc42 at protein levels.

Example 2

In Vivo Neuroprotection Assay for Nanoparticle-Carried miR-195

Male SD rats (280 to 350 g) were used for the induction of middle cerebral artery occlusion (MCAO) with previously reported surgical approaches (Candelario-Jalil, E. et al. *Effects of the cyclooxygenase-2 inhibitor nimesulide on cerebral infarction and neurological deficits induced by permanent middle cerebral artery occlusion in the rat. J. Neuroinflammation* 2, 3, 2005). A 3-0 nylon filament with silicon modification at the tip (Spratt, N. J. et al. *Modification of the method of thread manufacture improves stroke induction rate and reduces mortality after thread-occlusion of the middle cerebral artery in young or aged rats. J. Neurosci. Methods* 155, 285-290, 2006) was inserted into a small nick on the right common carotid artery (CCA) and advanced approximately 22 mm beyond the carotid bifurcation. Thereafter, surgical sutures were ligated along the CCA rostral to the nick to anchor the nylon filament and to seal off the vessel. The skin incision was closed with surgical suture and topically treated with antibiotic ointment. Nanoparticles have been advocated as an ideal drug carrier for diseases in the central nervous system because their small particle size makes them easier to pass through the brain blood barrier. Liposome nanoparticles were used to carry miR-195 as a more ideal drug carrier. In the study, a commercial liposome was used to carry miR-195. The commercial liposome nanoparticle is to incorporate miR-195 into a semi-dry formulation, which composed of natural lipid, non-ionic detergent, oil and small molecules, from the MaxSuppressor in vivo RNALancerII kit (BIOO Scientific, Inc.). Briefly, liposome emulsion and miR-195 (100 µg) are mixed in the presence of sterile RNase-Free 10×PBS (1:2 w/w miR-195-phospholipid-oil emulsion) in a single glass of the kit for a stock concentration of 10-20 mg/mL. To increase the efficiency of encapsulation and reduce the size of the liposomes, liposome emulsion is sonicated in an ultrasonic water bath for 5 min at room temperature.

The result from the nanoparticle experiment is promising and exciting. The detailed procedure is follow—formulated miR-195 carried by liposomes were administered intravenously (i.v.) by tail vein injections (a volume of 150 mm$^3$) 30 min or 2 hours after the induction of stroke by MCAO.

Twenty-four hours after treatment, rats were euthanized and decapitated. Rat brains were collected and sliced into 2 mm coronal sections, and stained with 0.1% 2,3,5-triphenyltetrazolium chloride (TTC) (Joshi, C. N., Jain, S. K. & Murthy, P. S. An optimized triphenyltetrazolium chloride method for identification of cerebral infarcts. Brain Res. 13, 11-17, 2004). Stained brain slices were scanned with a flatbed scanner. The infarct areas were measured and processed with ImageJ (version 1.40, NIH, Bethesda, Md., USA) according to the method of Lin et al (Lin, T. N., He, Y. Y, Wu, G., Khan, M. & Hsu, C. Y. *Effect of brain edema on infarct volume in a focal cerebral ischemia model in rats. Stroke* 24, 117-121, 1993).

Figure 8:
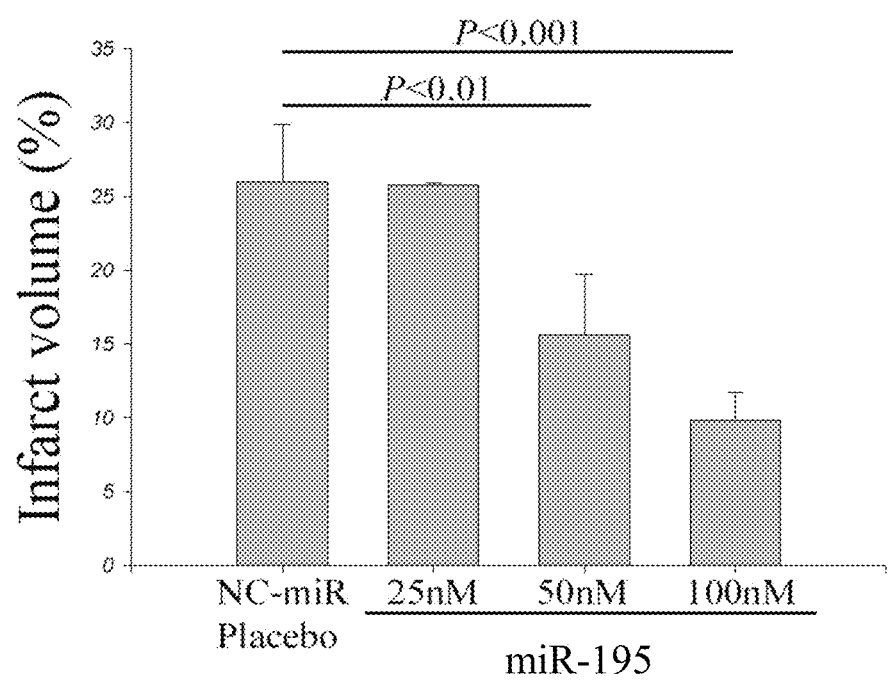
FIG. 8 shows a dose-dependent effect on reducing damaged brain after intravenous injection of liposome carried miR-195 (1.65-6.6 nanomole/kg; in the invention, 50 nM is equal to 3.3 nanomole/kg) in stroke rat 30 min after the induction of stroke. Quantitative presentation of infarct volume as percent of total brain volume. NC indicated a scrambled miR.
Figure 9:
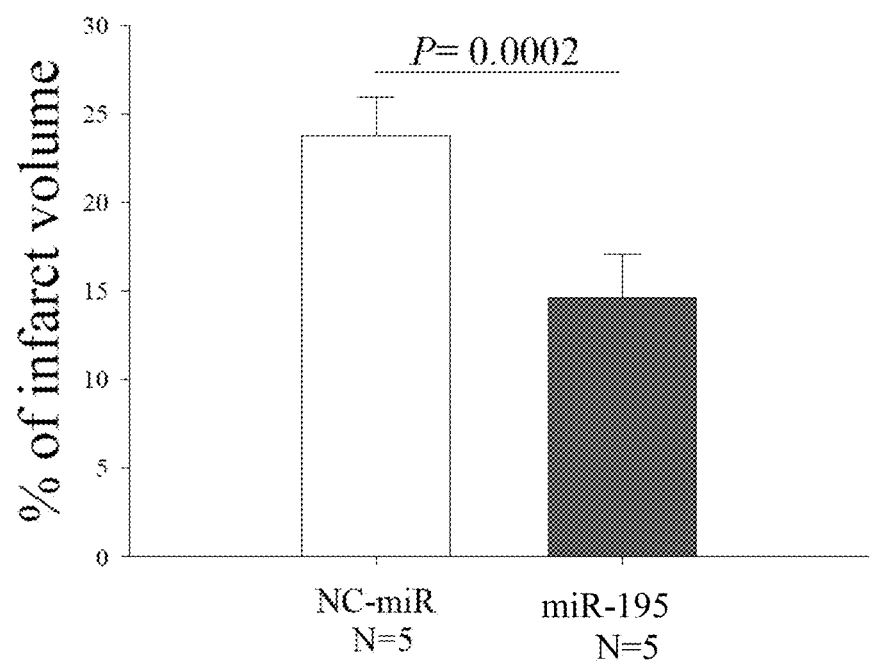
FIG. 9 shows intravenous injection of liposome carried miR-195 (3.3 nanomole/kg; un the invention, 50 nM is equal to 3.3 nanomole/kg) in stroke rat 120 min after the induction of stroke.

The infarct areas were measured. When miR-195 was administered 30 min after induction of stroke, the treatment can reduce the infarct volume by 40% with the dose of 3.3 nanomole/kg and by 60% with the does of 6.6 nanomole/kg (see FIG. 8). When miR-195 was administered 2 hours after induction of stroke, the treatment can still reduce the infarct volume by 40% with the dose of 3.3 nanomole/kg (FIG. 9).

Figure 10:
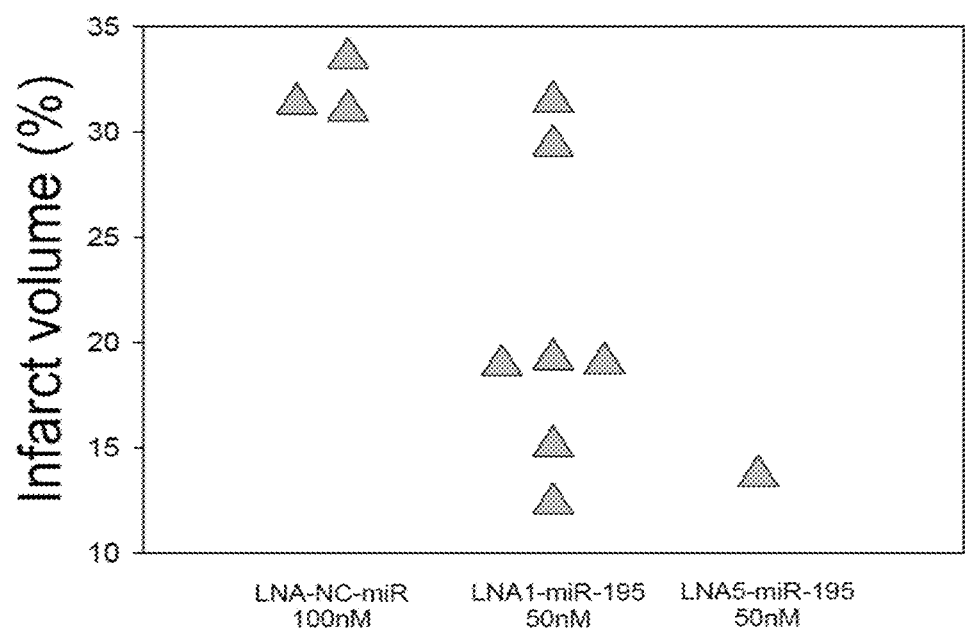
FIG. 10 shows intravenous injection of LNA1 in stroke rat 30. Quantitative presentation of infarct volume as percent of total brain volume. NC indicated a scrambled miR.

The LNA-modified microRNA 195s of the invention were used in the treatment of stroke rats according to the above-mentioned in vivo neuroprotection assay in rats. The results show that LNA-modified microRNA 195s (such as LNA1, LNA2, LNA3, LNA4 and LNA5) provides signification therapectic efficacy. As shown in FIG. 10, the mean therapeutic effect by LNA1 is to reduce the infarct volume by 30% and LNA5 can even reduce the infarct volume by 58% when compared to the scramble LNA-NC-miR.

What is claimed is:

1. A method for treating a subject suffering from neuronal or brain injury or neurodegenerative diseases, comprising administering to the subject an effective amount of a microRNA selected from a miRNA-195, a modified miRNA-195 and a combination thereof.

2. The method of claim 1, wherein the miRNA is miRNA-195.

3. The method of claim 1, wherein the modified miRNA-195 is LNA modified miRNA-195.

4. The method of claim 1, wherein the miRNA has the sequence selected from SEQ ID NO: 1-7.

5. The method of claim 1, wherein the miRNA has the sequence of SEQ ID NO: 1 or SEQ ID NO: 2.

6. The method of claim 1, wherein the miRNA-195 is in an amount ranging from 1.0 to 10.0 nanomole/kg.

7. The method of claim 1, wherein the miRNA-195 is in an amount ranging from 3.0 to 10.0 nanomole/kg.

8. The method of claim 1, wherein the miRNA-195 is miRNA-195 mimic, the miRNA-195 mimic is synthetic miRNA-195 duplex.

9. The method of claim 1, wherein the miRNA can be combined with a nanoparticle.

10. The method of claim 9, wherein the nanoparticle is liposome, micelle, metal nanoparticle, or polymeric nanoparticle.

11. The method of claim 9, wherein the nanoparticle is liposome.

12. The method of claim 1, wherein the neuroprotection is through inhibition of Sema3 A expression or accumulation.

13. The method of claim 1, wherein the neuroprotection is through inhibition or prevention of neuron apoptosis.

14. The method of claim 1, wherein the neuroprotection is through anti-inflammatory effect for protecting neurons against cellular stresses.

15. The method of claim 14, wherein the stress is an excitotoxicity stress, an oxidative stress, or a stress caused by spinal cord damage, ataxia or alcoholism.

16. The method of claim 1, wherein the neuroprotection is through reduction of overproduction of NO.

17. The method of claim 1, wherein the miRNA is used as free radical scavenger or anti-inflammatory drug.

18. The method of claim 1, wherein the neurodegenerative disease is acute or chronic neurodegenerative disease.

19. The method of claim 1, wherein the treatment is associated with cerebrovascular insufficiency, focal or diffuse brain trauma, spinal cord injury, cerebral ischemia or infarction, Parkinson's disease, Huntington's disease, amyotrophic lateral sclerosis, Alzheimer's disease, Rett Syndrome, lysosomal storage disease or multiple sclerosis, hypoxia, spinal cord injury, peripheral nerve injury or stroke.

20. The method of claim 19, wherein the cerebral ischemia or infarction is emolic occlusion and thrombotic occlusion, perinatal hypoxic-ischemia, neonatal hypoxia-ischaemic encephalopathy, perinatal asphyxia, cardiac arrest, intracranial hemorrhage, subarachnoid hemorrhage, stroke, or traumatic brain injury.

21. The method of claim 20, wherein the stroke is ischemic stroke.

* * * * *

SEQUENCE LISTING

<160> NUMBER OF SEQ ID NOS: 7

<210> SEQ ID NO 1
<211> LENGTH: 21
<212> TYPE: RNA
<213> ORGANISM: Homo sapiens

<400> SEQUENCE: 1
uagcagcaca gaaauauugg c                                              21

<210> SEQ ID NO 2
<211> LENGTH: 87
<212> TYPE: RNA
<213> ORGANISM: Homo sapiens

<400> SEQUENCE: 2
agcuucccug gcucuagcag cacagaaaua uuggcacagg gaagcgaguc ugccaauauu    60
ggcugugcug cuccaggcag gguggug                                        87

<210> SEQ ID NO 3
<211> LENGTH: 21
<212> TYPE: RNA
<213> ORGANISM: Artificial
<220> FEATURE:
<223> OTHER INFORMATION: Designed nucleic acid based on Human miRNA-195
      with LNA modified
<220> FEATURE:
<221> NAME/KEY: misc_feature
<222> LOCATION: (20)..(20)
<223> OTHER INFORMATION: LNA modified
<220> FEATURE:
<221> NAME/KEY: misc_feature
<222> LOCATION: (21)..(21)
<223> OTHER INFORMATION: LNA modified

<400> SEQUENCE: 3
uagcagcaca gaaauauugg c                                              21

<210> SEQ ID NO 4
<211> LENGTH: 21
<212> TYPE: DNA
<213> ORGANISM: Artificial
<220> FEATURE:
<223> OTHER INFORMATION: Designed nucleic acid based on Human miRNA-195
      with LNA modified
<220> FEATURE:
<221> NAME/KEY: misc_feature
<222> LOCATION: (1)..(1)
<223> OTHER INFORMATION: LNA modified
<220> FEATURE:
<221> NAME/KEY: misc_feature
<222> LOCATION: (20)..(20)
<223> OTHER INFORMATION: LNA modified
<220> FEATURE:
<221> NAME/KEY: misc_feature
<222> LOCATION: (21)..(21)
<223> OTHER INFORMATION: LNA modified

<400> SEQUENCE: 4
tagcagcaca gaaauauugg c                                              21

<210> SEQ ID NO 5
<211> LENGTH: 21
<212> TYPE: DNA
<213> ORGANISM: Artificial
<220> FEATURE:
<223> OTHER INFORMATION: Designed nucleic acid based on Human miRNA-195
      with LNA modified
<220> FEATURE:

```
<221> NAME/KEY: misc_feature
<222> LOCATION: (1)..(1)
<223> OTHER INFORMATION: LNA modified
<220> FEATURE:
<221> NAME/KEY: misc_feature
<222> LOCATION: (15)..(15)
<223> OTHER INFORMATION: LNA modified
<220> FEATURE:
<221> NAME/KEY: misc_feature
<222> LOCATION: (17)..(17)
<223> OTHER INFORMATION: LNA modified
<220> FEATURE:
<221> NAME/KEY: misc_feature
<222> LOCATION: (18)..(18)
<223> OTHER INFORMATION: LNA modified
<220> FEATURE:
<221> NAME/KEY: misc_feature
<222> LOCATION: (20)..(20)
<223> OTHER INFORMATION: LNA modified
<220> FEATURE:
<221> NAME/KEY: misc_feature
<222> LOCATION: (21)..(21)
<223> OTHER INFORMATION: LNA modified

<400> SEQUENCE: 5
tagcagcaca gaaatattgg c                                              21

<210> SEQ ID NO 6
<211> LENGTH: 21
<212> TYPE: DNA
<213> ORGANISM: Artificial
<220> FEATURE:
<223> OTHER INFORMATION: Designed nucleic acid based on Human miRNA-195
      with LNA modified
<220> FEATURE:
<221> NAME/KEY: misc_feature
<222> LOCATION: (1)..(1)
<223> OTHER INFORMATION: LNA modified
<220> FEATURE:
<221> NAME/KEY: misc_feature
<222> LOCATION: (2)..(2)
<223> OTHER INFORMATION: LNA modified
<220> FEATURE:
<221> NAME/KEY: misc_feature
<222> LOCATION: (5)..(5)
<223> OTHER INFORMATION: LNA modified
<220> FEATURE:
<221> NAME/KEY: misc_feature
<222> LOCATION: (10)..(10)
<223> OTHER INFORMATION: LNA modified
<220> FEATURE:
<221> NAME/KEY: misc_feature
<222> LOCATION: (15)..(15)
<223> OTHER INFORMATION: LNA modified
<220> FEATURE:
<221> NAME/KEY: misc_feature
<222> LOCATION: (17)..(17)
<223> OTHER INFORMATION: LNA modified
<220> FEATURE:
<221> NAME/KEY: misc_feature
<222> LOCATION: (18)..(18)
<223> OTHER INFORMATION: LNA modified
<220> FEATURE:
<221> NAME/KEY: misc_feature
<222> LOCATION: (20)..(20)
<223> OTHER INFORMATION: LNA modified
<220> FEATURE:
<221> NAME/KEY: misc_feature
<222> LOCATION: (21)..(21)
<223> OTHER INFORMATION: LNA modified

<400> SEQUENCE: 6
tagcagcaca gaaatattgg c                                              21

<210> SEQ ID NO 7
```

```
<211> LENGTH: 21
<212> TYPE: DNA
<213> ORGANISM: Artificial
<220> FEATURE:
<223> OTHER INFORMATION: Designed nucleic acid based on Human miRNA-195
      with LNA modified
<220> FEATURE:
<221> NAME/KEY: misc_feature
<222> LOCATION: (2)..(2)
<223> OTHER INFORMATION: LNA modified
<220> FEATURE:
<221> NAME/KEY: misc_feature
<222> LOCATION: (5)..(5)
<223> OTHER INFORMATION: LNA modified
<220> FEATURE:
<221> NAME/KEY: misc_feature
<222> LOCATION: (10)..(10)
<223> OTHER INFORMATION: LNA modified
<220> FEATURE:
<221> NAME/KEY: misc_feature
<222> LOCATION: (15)..(15)
<223> OTHER INFORMATION: LNA modified
<220> FEATURE:
<221> NAME/KEY: misc_feature
<222> LOCATION: (17)..(17)
<223> OTHER INFORMATION: LNA modified
<220> FEATURE:
<221> NAME/KEY: misc_feature
<222> LOCATION: (18)..(18)
<223> OTHER INFORMATION: LNA modified
<220> FEATURE:
<221> NAME/KEY: misc_feature
<222> LOCATION: (20)..(20)
<223> OTHER INFORMATION: LNA modified
<220> FEATURE:
<221> NAME/KEY: misc_feature
<222> LOCATION: (21)..(21)
<223> OTHER INFORMATION: LNA modified

<400> SEQUENCE: 7
tagcagcaca gaaatattgg c                                              21
```